United States Patent [19]

Brehm et al.

[11] Patent Number: 5,157,960
[45] Date of Patent: Oct. 27, 1992

[54] METHOD AND APPARATUS FOR TRANSIENT MEASUREMENT OF GAS PERMEABILITY IN CLOSED-CELL FOAM INSULATION

[75] Inventors: Timothy R. Brehm, Seattle, Wash.; Leon R. Glicksman, Lynnfield, Mass.

[73] Assignee: Massachusetts Institute of Technology, Cambridge, Mass.

[21] Appl. No.: 475,659

[22] Filed: Feb. 6, 1990

[51] Int. Cl.⁵ .................................. G01N 15/08
[52] U.S. Cl. ..................................... 73/38
[58] Field of Search ........................... 73/38

[56] References Cited

U.S. PATENT DOCUMENTS

| | | | |
|---|---|---|---|
| 3,301,043 | 1/1967 | Lyssy | 73/38 |
| 3,548,634 | 12/1970 | Roy | 73/38 |
| 4,304,122 | 12/1981 | Tentor | 73/38 |
| 4,385,517 | 5/1983 | Sorce et al. | 73/38 |
| 4,489,593 | 12/1984 | Pieters et al. | 73/38 |
| 4,531,404 | 7/1985 | Phelps et al. | 73/38 |
| 4,555,934 | 12/1985 | Freeman et al. | 73/38 |
| 4,662,214 | 5/1987 | Heitmann et al. | 73/38 |
| 4,718,270 | 1/1988 | Storr | 73/38 |
| 4,762,010 | 9/1988 | Borghard et al. | 73/38 |

FOREIGN PATENT DOCUMENTS 386320 6/1973 U.S.S.R. .

OTHER PUBLICATIONS

Brehm, M. S., Thesis submitted Feb. 6, 1990.
Carman, P. C. and Haul, R. A. W. (1954) *Proc. Royal Soc. London*, Section A, 222, pp. 109-118.

Primary Examiner—Hezron E. Williams
Assistant Examiner—George M. Dombroske
Attorney, Agent, or Firm—Bromberg & Sunstein

[57] ABSTRACT

Method and apparatus are provided for accurately and more rapidly measuring the permeability of various test gases in cellular polymeric materials with very low permeation rates, comprising a constant volume test chamber sealed with indium gaskets, said chamber being connected to a gas inlet valve and test gas reservoir with pressure gauge, gas outlet valve and oil check valve, an absolute pressure transducer to track the change in pressure in the test chamber, and said chamber being submerged in a water bath for strict temperature control. A thinly cut foam sample is placed in the test chamber surrounded by the test gas, where the gas inside the sample is first allowed to reach equilibrium with the surrounding gas; the pressure of the surrounding gas is then raised or lowered, and the rate at which the sample takes up or gives off the test gas is recorded over time as a change in pressure of the test gas around the foam. From this pressure variation the desired permeability coefficient may be measured, and achieved more quickly due to the reduced thickness of the sample. Unlike standard prior art transmission-method devices, this new sorption method and apparatus also allows for separate determination of the diffusion and solubility coefficients; it further allows for the use of much thinner foam samples than can be reliably used in prior art methods, resulting in a substantial reduction in testing time. The effective diffusion coefficient is used as an input to a computational model which predicts the rate of aging in a foam insulation panel. The effective solubility coefficient is used primarily to understand the behavior of the blowing agent in the foam system.

12 Claims, 11 Drawing Sheets

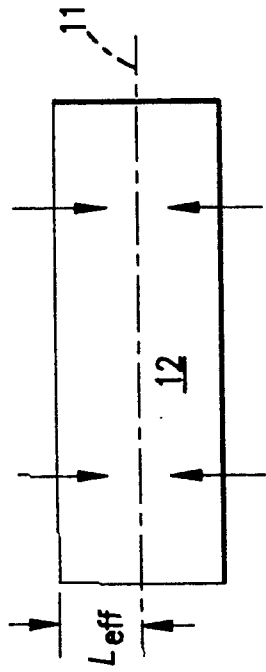
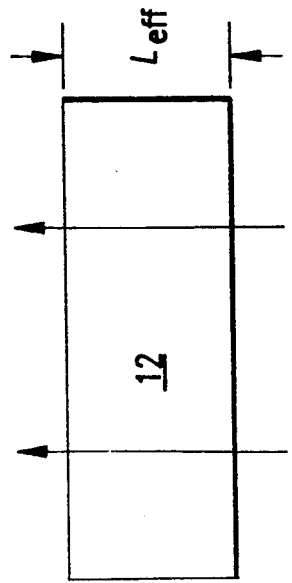
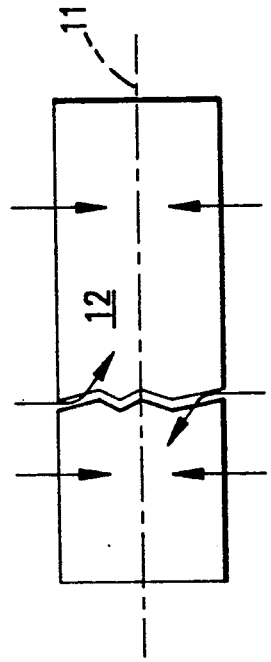
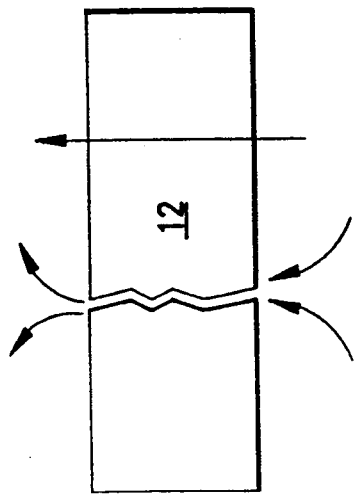

METHOD AND APPARATUS FOR TRANSIENT MEASUREMENT OF GAS PERMEABILITY IN CLOSED-CELL FOAM INSULATION

TECHNICAL FIELD

The present invention relates to methods and apparatus for measuring gas permeability of materials, and in particular cellular polymeric materials, such as closed-cell foam insulation.

BACKGROUND ART

Our interest in the problem of permeability measurement arises out of the closed-cell foam insulation industry. Closed-cell foam products have been used to great advantage in a wide variety of industrial applications due to their extremely low thermal conductivity, but they have always been subject to a little understood and poorly quantified aging phenomenon in which a foam's thermal properties degrade over time. Our objective has been to quantify the speed of the aging process and thereby assist industry in developing foams which are more resistant to this process.

The insulating value of a closed-cell foam depends largely on the thermal conductivity of the gas mixture which fills the cells of the foam. When the foam is first produced, the cells are filled with the blowing agent, usually a fluorocarbon gas, which has a low thermal conductivity (typically about one-third of that for stagnant air). As the foam is exposed to the environment over time, the component gases of air permeate into the cells of the foam and gradually dilute the fluorocarbon gas, producing a mixture which has a higher thermal conductivity than the fluorocarbon alone. Eventually the fluorocarbon gas permeates out of the foam, causing a further increase in the thermal conductivity of the remaining gas mixture. As this aging process occurs, the overall thermal conductivity of the foam rises and the insulating value of the foam drops proportionately. The time scales of this aging process can be quantified if the rates of permeation, in the form of the respective "permeability coefficient", of the air components and the fluorocarbon blowing agents are known. The two central components of permeability are the diffusion coefficient, which quantifies transient transport processes, and the solubility coefficient, which characterizes steady-state storage capacity.

The main difficulty in determining these permeability coefficients is the amount of time required to obtain accurate measurements. In systems with low diffusion rates, the measurement of these coefficients is extremely time-consuming. In systems with low solubilities, the measuring apparatus must be very sensitive to produce meaningful results. Closed-cell foam insulation is an example of a system with both low diffusion rates and low solubilities and it therefore presents one of the most challenging applications for these types of measurements. Typical times required to measure the permeability of one gas species in one foam sample have been on the order of weeks to months using currently available techniques. Polymer chemists developing new aging-resistant foams need this data as quickly as possible to make the most useful progress.

One drawback of these foam products is their use of chlorofluorocarbons, or CFCs, which have recently been linked to the degradation of the Earth's ozone layer. The foam manufacturing process relies on the unique thermodynamic properties of the CFC to act as a "blowing agent", which expands and inflates the polymeric mixture as the mixture changes phase from liquid to solid, thereby forming the cellular foam structure. This process produces a foam whose cells are filled with CFC vapor. During the service life of the foam or when the foam is destroyed, this vapor may be released into the atmosphere and subsequently contribute to the ozone degradation. Fortunately this problem has received attention on an international scale which has led to a scheduled phasing out of the use of the CFC products which are known to be harmful. Researchers in the industry have responded with efforts to find replacements for the banned CFCs. To aid this research for a replacement, industry needs a tool for more rapidly and accurately assessing the characteristics of new blowing agents and the related foam products.

1. Industry Accelerated Aging Test

In order to quantify the relative aging rates of closed-cell foams, the industry has attempted to use the Accelerated Aging Test, so called because it takes advantage of the increase in permeation rates with temperature to accelerate the aging process. In the test, a fresh foam sample is maintained in a 40° C. environment for 90 to 180 days. The overall thermal conductivity of the sample is measured before and after this exposure and the difference is taken as an indication of the foam's resistance to aging.

This test is useful to industry because it distinguishes foam aging characteristics on a relative scale, but from a broader point of view the test has several major drawbacks. The central problem is that the effect of temperature on aging rates is not known exactly, so it is difficult to relate the aging that occurs during the accelerated test to that which might occur in some specified operating conditions other than a constant 40° C. For example, Ostrogorsky, A. G., "Aging of Polyurethane Foams" Ph.D. Thesis, Department of Mechanical Engineering, Massachusetts Institute of Technology, 1985, recently found that the increase in the permeation rate of the blowing agent for a given increase in temperature is larger than that of the air components. The test also does not give any insight into the physics of the aging process which might enable the development of superior foams. Furthermore, although it is accelerated relative to the normal aging time scale, it is still too slow to provide timely feedback on foam quality in attempts to improve foam aging characteristics by empirical means.

2. General Model of Foam Aging Process

The first step in understanding the foam aging process is the development of a model which quantifies the relationship between gas permeation and changes in thermal conductivity. Cuddihy, E. F., and Moacanin, J., "Diffusion of Gases in Polymeric Foams", *Journal of Cellular Plastics*, vol. 3, Feb. 1963, pp. 73-80, first demonstrated that closed-cell foam can be treated as a homogeneous medium which obeys Fick's first law of diffusion (see Brehm Thesis, Section 2.1.3). If the diffusion coefficient is assumed to be independent of concentration, then the time-dependent gas concentration in the foam may be modelled by Fick's second law with uniform initial conditions and constant boundary conditions. The solution of this model was first given by Newman, A. B., "The Drying of Porous Solids: Diffusion Calculations", *Transactions of the American Institute of Chemical Engineers*, 27, 1931, p.310, for a slab geometry and has been presented by Carslaw, H. S., and Jaeger, J. S., The Conduction of Heat in Solids, Oxford University Press, Oxford, England, 1959, and by Arpaci, V. S., Conduction Heat Transfer, Addison-Wesley Publishing Co., Reading, MA, 1966 for a variety of other geometries and initial conditions. If the diffusion coefficient is known for each gas, these solutions may be used to predict the variation in a foam's cell gas composition with time.

A review of models for the thermal conductivity of gas compositions is given by Tsederberg, N. V., Thermal Conductivity of Gases and Liquids, The MIT Press, Cambridge, MA, 1965. Schuetz, M. A., "Heat Transfer in Foam Insulation", M. S. Thesis, Department of Mechanical Engineering, Massachusetts Institute of Technology, 1982, used an equation with empirical corrections proposed by Lindsey and Bromley, presented by Tsederberg, to calculate the thermal conductivity of the cell gas mixture. He proposed calculating the thermal conductivity of the gas composition at several positions in the foam to find an effective thermal conductivity for the foam gas mixture.

Ostrosgorsky, supra, presented a numerical simulation of Fick's law applied to a foam panel in which the initial gas concentrations may be prescribed and a temperature profile may be imposed. He followed Schuetz in calculation of the thermal conductivity of the cell gas mixture and assumed an Arrhenius-type variation of gas permeability with temperature. If the constants from this Arrhenius equation are given for each gas, the simulation predicts the increase in the overall thermal conductivity of a foam panel as a function of time.

It is important to realize that each of the models requires the diffusion and solubility coefficients of the air components and the blowing agent in the foam to predict the rate of thermal aging.

3. Geometric Models and Measurement Techniques

Since the polymer cell walls are the controlling factor in the gas permeation process, much effort has been focussed on measuring the geometric characteristics of the cell structure and modelling the effects which this structure has on the overall permeability of the foam. The first model of this type was developed by Cuddihy and Moacanin, supra, and is based on one-dimensional flow through a cubical cell structure with uniform wall thickness. Valenzuela and Glicksman, "Thermal Resistance and Aging of Rigid Urethane Foam Insulation, *Proceedings of DOE-ONRL Workshop on Mathematical Modelling of Roofs*, Atlanta, GA, CONF-811179, Nov. 3-4, 1981, p. 261, showed that slight changes in this geometry, e.g. staggering the cells, may change the results by as much as 100%.

The first quantitative characterization of foam cell structure was done by Reitz, D. W., "A Basic Study of Gas Diffusion in Foam Insulation", M. S. Thesis, Department of Mechanical Engineering, Massachusetts Institute of Technology, 1983, using an innovative sectioning technique. Based on his measurements and some correlation with permeability measurements, he concluded that cell wall thickness, polymer permeability, and foam density are the most important parameters for predicting foam aging, while the effects of assumed cell structure are of secondary importance. He also demonstrated that only 10-20% of the solid polymer in a typical polyurethane foam is in the cell walls, with the remaining 80-90% in the struts which form at the intersections of cell walls. Ostrogorsky, supra, refined Reitz's model by adding a geometrical enhancement parameter and verified the model using a two-dimensional electrical analogy. His results correlate well with his measurements of permeability in foams and in polymer films which were assumed to be representative of cell walls. Fox, T. J., "Aging of Closed-Cell Phenolic Foam", M. S. Thesis, Department of Mechanical Engineering, Massachusetts Institute of Technology, 1986, applied a similar model to the study of phenolic foams and used Scanning Electron Microscope photography to improve the geometric measurement technique.

Two particularly valuable results have come from this study of the microscopic structure of the foam. The first is the ability to make an estimate of foam permeability based on measurements of cell wall permeability and the relatively straightforward measurements of the foam geometry. This is especially useful when comparing the performance of foams which have similar polymer composition but may, for example, vary in cell size or cell wall thickness. The second valuable result of the geometric models is the ability to translate from the permeability of the foam to the permeability of the cell wall, and vice versa. This gives the experimenter the freedom to measure either quantity and readily obtain insight into the other as well. As permeability measurements of either the foam or the polymer are very difficult and time-consuming, any added flexibility such as this can be very advantageous.

The gas permeation models and geometric models all rely on the ability to measure either the permeability of the solid polymer or the effective permeability of the foam. Because of extremely low permeation rates, especially for the CFC blowing agents, these measurements have proven rather difficult and extremely time-consuming. The large variation in the published data for foam effective diffusion coefficients, shown in Table 1, implies the need for more accurate measurement techniques, while the scarcity of this type of data indicates the need for faster test methods.

TABLE 1

Summary of Published Data for Effective Diffusion Coefficients of $O_2$, $N_2$, and R11 in Urethane Foams at 25 C.

| FOAM DENSITY [kg/m$^3$] | DIFFUSION COEFFICIENT [$10^{-8}$ cm$^2$/sec] | | | SOURCE* |
|---|---|---|---|---|
| | $O_2$ | $N_2$ | R11 | |
| 33.5 | 200. | 100. | 3.0 | Ball |
| 35.9 | 4.0-7.0 | 5.5-16. | .006-.25 | Brandreth |
| 33.5 | 6.0 | 2.0-3.0 | .025-.046 | Brandreth |
| 35.2 | 11.2 | 6.3 | .225 | Norton |
| 35.2 | — | — | .042 | Norton |
| 24.5 | 196. | — | — | Lee |
| 25.6 | 148. | — | — | Lee |
| 20.7 | 76.8 | — | — | Reitz |
| 28.3 | 119. | — | — | Reitz |
| 30.4 | 193. | — | — | Reitz |
| 25.2 | 46.8* | 7.6 | .23-.57 | Ostrogorsky |

*References: Ball, G. W., Hard, R., Walker, M. G., "The Thermal Conductivity of Rigid Urethane Foams", Journal of Cellular Plastics, 1970; Brandreth, D. A., Ingersole, H. G., "Accelerated Aging of Rigid Polyurethane Foam", Unpublished Report, E. I. Dupont de Nemours and Co., Wilmington, Delaware; Norton, F. J., "Diffusion of Chlorofluorocarbon Gases in Polymer Films and Foams", Journal of Cellular Plastics, 1982, p. 300; Lee, W. M., Brown, C. N., "Gas Permeability Determination in Urethane Foams", Journal of Thermal Insulation, vol. 6, 1983; Reitz, supra; Ostrogorsky, supra.

4. Current Permeability Measurement Techniques: Transmission vs. Sorption/Desorption Currently the most commonly used techniques of computing gas permeability through closed-cell foam insulation can be divided into two categories: transmission methods, and sorption/desorption methods. The latter method is used in the present invention.

In the transmission method, the material to be tested is placed between two isolated chambers which contain different pressures of the test gas. When the gas flow rate from the high pressure side to the low pressure side has reached a steady state, this flow rate is measured and the value is used to calculate the desired permeability coefficient. The gas flow is generally measured by recording either a constant-pressure volume change, or a constant-volume pressure change on the low pressure side of the material. Such a transmission system is basically described in S. K. Roy, "Permeability Cell", U.S. Pat. No. 3,548,634, Dec. 22, 1970, as applied to ceramics for the purpose of obtaining information on its internal pore characteristics. Other detection techniques have been used in transmission methods, including laser spectroscopy, gas chromatography and flame ionization, but most of these are expensive, cumbersome, and limited in application.

With a sorption/desorption method as practiced in the prior art, the material to be tested is placed in a chamber in which it is surrounded by the test gas. Before the test begins, the concentration of the gas inside the material is allowed to come to equilibrium with the pressure of the gas in the chamber. To begin the test, the pressure of the surrounding gas is suddenly changed (increased for sorption, decreased for desorption), and the rate at which the material takes up or gives off the test gas is recorded. From the measured sorption/desorption rate, the diffusion coefficient is determined, and from the equilibrium gas uptake the solubility coefficient is found. In most cases the gas uptake is recorded by "gravimetric" means, in which the pressure of the test gas around the material is held constant while the increase in weight of the sample is recorded.

The general concept of a constant-volume sorption method of measuring diffusion coefficients appears to have been first proposed by Carman and Haul, in Proceedings of the Royal Society of London, Section A, volume 222, pp. 109–118 (1954). Their paper suggests the general method and discusses some of the mathematical analysis, but it gives no structure whatever for implementing this method or reducing it to practice. That paper presents some data obtained solely in using the method to measure gas adsorption in solid silica material with moderate permeation rates.

SUMMARY OF THE INVENTION AND GENERAL CONSIDERATIONS

The present invention achieves a significant advance in the field of permeability by the reduction to practice of the sorption method to practice for the difficult application of gas permeation in closed-cell foams with very low permeation rates. The invention is further described in "Transient Measurement of Gas Permeability in Closed Cell Foam Insulation", M. S. Thesis, Department of Mechanical Engineering, Massachusetts Institute of Technology, 1988, by Timothy R. Brehm, a co-inventor herein, which work (hereinafter called the "Brehm Thesis") is a part of the file of the application herein and is incorporated herein by reference. In accordance with the present invention, a method and apparatus are provided for more rapidly measuring the permeability of various gases through materials including those with low permeability such as closed-cell foam insulation. Unlike prior art systems, which generally rely on steady state techniques, the basis of the present invention is the measurement of the transient pressure in an isolated, constant-volume chamber containing the sample and the test gas, immediately after the test gas pressure surrounding the sample has been increased (for adsorption) or decreased (for desorption) in a step fashion. The transient diffusion equation for the appropriate sample-chamber geometry is solved and the solution is used to generate the effective diffusion and solubility coefficients from the transient pressure curve. For all the prior art methods mentioned above, the time to complete a single measurement depends largely on the thickness (or other relevant physical dimension) of the sample being tested. The method and apparatus of in the present invention reduces testing time primarily by allowing the use of samples which are substantially thinner than those used with other methods. In addition, unlike standard prior art transmission-type devices, the herein disclosed sorption method and apparatus determines the effective diffusion coefficient and the effective solubility coefficients independently in a single test. The effective diffusion coefficient is used as an input to a computational model which predicts the rate of aging in a foam insulation panel. (It will be understood that although the present discussion may refer to a "foam sample", the invention is applicable to nearly any material the permeability of which is sought to be measured, but is particularly valuable with respect to materials having relatively low permeability.) The effective solubility coefficient is used, among other things, to understand the behavior of the blowing agent in the foam system, and therefore is of particular interest in the screening of alternative non-CFC blowing agents.

1. Sample Thickness

Since the diffusion coefficient is fixed for a given foam sample, test gas and temperature, the only way to reduce time consumed for a test at a given temperature is to reduce the sample thickness. Prior art transmission-type measurements as shown in FIG. 1A, force the test gas through the sample 12 by applying different pressures on the two faces, so that the gas permeates into one side of the sample and out of the other side. The present invention, on the other hand, permits a decrease in sample thickness because (as shown in FIG. 1B,) the test gas surrounds the sample 12 with some uniform pressure, and permeates into the sample equally from both sides (neglecting edges and non-slab geometries).

This qualitative difference allows reduction of sample thickness in two ways. First, the fact that the gas is diffusing into the sample from both sides cuts the effective sample thickness $L_{eff}$ in half of the same physical sample thickness. The effective thickness may be thought of as the longest distance a gas molecule must travel in the foam to attain complete permeation. Since molecules from both sides of the sample will permeate at equal rates, none has to go past the sample center line 11 to accomplish this end. Thus the effective thickness is the distance from either surface to the center line, or one half of the physical sample thickness. In a transmission-type apparatus each molecule must diffuse all the way from one side of the sample to the other, so the effective thickness is exactly equal to the physical sample thickness.

The second manner in which the "surrounding gas" method improves on the "through-flowing gas" method results from the possible existence of defects in the foam sample's cell structure. As shown in FIG. 2A, in a transmission-type measurement, the gas will tend to take the path of least resistance from one side of the sample to the other, so if there is a series of cracks or pinholes that provide a path all the way or almost all the way through the sample 12, the accuracy of the measurement is destroyed. To reduce this possibility, the foam sample must be fairly thick, typically on the order of 30 to 40 cell diameters or more. As shown in FIG. 2B in the sorption process, however, potential cracks or pinholes forming a pathway across the sample 12 connect two regions of test gas that are at the same pressure, so there is no driving force for gas to flow through such a pathway. The defect would represent an increase in the surface area of sample exposed to the test gas and a slight change in the geometry of diffusion within the foam, but the resulting inaccuracies should be relatively small and are corrected to some degree by the technique which is used to measure the sample thickness. (see "Two Dimensional Analysis" in the Detailed Description below and Section 5.1.1 of the Brehm Thesis) Therefore, the samples used in the transient technique may be considerably thinner, limited only by the need to adequately represent the foam structure, which may typically be satisfied by a thickness equal to approximately 10 to 15 foam cell diameters. Typical cell diameters for polyurethane foams are on the order of 0.03 cm, so in a preferred embodiment the test chamber is designed to accept samples with thicknesses up to 0.50 cm. The shape of the sample in cross-section is largely dictated by the method of foam sample preparation and by considerations relating to fabricating the test chamber. Both of these factors tend to favor a circular cross-section. Thus, the transient tests in accordance with the present invention have been performed to date with samples that are typically half as thick as required for reliable transmission measurements. This fact together with the fact that the transient test herein allows gas to permeate toward the sample's centerline from both sides, yields an effective sample thickness of one-fourth of that for comparable transmission measurement. With an understanding of the non-dimensional time scale over which diffusions occurs, $\tau 32\,Dt/L^2$, where L is the sample thickness and D is the diffusion coefficient at the sample's temperature (See "Basic Model" in "Data Analysis" below in the Detailed Description as well as Section 2.3.2 of the Brehm Thesis) one can see that the resulting transient test at any given temperature will then be $4^2$ or 16 times faster than the comparable transmission test. Transient tests are possible with even thinner samples, perhaps as thin as half of what has been used in the first round of tests, giving a factor of 64 in test-to-test comparison with currently used transmission methods.

2. Using Solubility to Further Reduce Testing Time

Another technique for accelerating permeability testing is to circumvent the diffusion time constant by devising a method in which the system does not have to change completely from one equilibrium state to another. For example, a standard transmission-type apparatus is usually used to measure the gas flow rate through a foam sample after the sample has changed from the zero-flow equilibrium state, in which the pressures on its two faces are equal, to a constant-flow equilibrium state, in which different pressures on its two faces have been imposed and enough time has passed (approximately $L^2/D$) to develop a linear concentration profile across the sample and produce the resulting constant flow rate. This same apparatus could be used to calculate a diffusion coefficient from measurement of flow rates after the pressure difference is imposed but before the final equilibrium state is reached, with the test time correspondingly reduced, *if the solubility coefficient is known*. Ostragorsky, supra. The transmission measurement provides no way, however, to measure solubility.

The ability of the present invention to separately measure this solubility coefficient allows it to take advantage of this shortcut to further achieve the objective of decreasing the required test time. As discussed further under "Accelerated Determination of D" in the Detailed Description below (see also Brehm Thesis, Section 5.1.4, for more detailed discussion), if the solubility is measured for a given gas and foam in a relatively fast high temperature test, it may be used to predict the solubility at other temperatures, thereby allowing the tests at these other temperatures to be completed in about one-fourth the time that would be otherwise be required. It can be seen that in combining the benefits of effective reduction in sample thickness (reduction by a factor of about 16 to 64 in testing time) with the use of solubility coefficient measurement (reduction by a factor of about 4 in testing time), the present invention can typically reduce testing time by a factor of about 64 to 256.

3. Constant Volume Vs. Constant-Pressure

The main difference between the method of the present invention and other sorption-desorption techniques is the means of measurement of the rate of sorption. Most transient methods maintain a constant pressure of the test gas around the sample and measure the sorption rate via gravimetric analysis (i.e., follow the weight increase of the sample). In principle the gravimetric analysis is straightforward, and indeed it has been used successfully in many applications where the diffusion rates and/or the solubility levels are high. For the more difficult application to very low diffusion rates and solubility levels, however this method has proven to be extremely difficult to reduce to practice. The alternative offered by the present invention is to maintain a sealed, constant-volume chamber surrounding the foam, so that the total mass in the system is constant and the pressure drop in the chamber indicates the rate of mass uptake by the sample. In general, this measurement is more convenient and more accurate than the gravimetric analysis. The sensitivity of the constant-volume apparatus may be adjusted by altering the geometry of the chamber and the sample, discussed in greater detail below. The solution of the equations for the constant-volume boundary condition is a bit more involved than that for the more common constant-pressure condition, but it is just as easily applied to calculate the desired coefficients.

Unfortunately, in practice the sorption/desorption method using a "gravimetric" detection system is also hampered by sensitivity problems related to thin samples. As the sample is cut thinner, the mass uptake per unit sample area decreases, making accurate measurement of the sample weight increase very difficult, especially over the relatively long time periods associated with permeation in closed-cell foams. However, in the constant-volume sorption/desorption apparatus in accordance with the present invention, the sensitivity to reduced uptake levels is easily maintained by reduction of the free volume of gas surrounding the foam. For any decrease in sample thickness, the gas volume may be decreased proportionately through the use of specially designed spacers, taking advantage of the physical principle that pressure changes at constant volume are easily followed.

4. Test Chamber Sensitivity

With the sample thickness constrained by considerations of test duration, the remaining internal dimensions of the test chamber, including the sample cross-sectional area and the volume of all adjoining spaces, are designed to maximize test chamber sensitivity. This sensitivity is judged with respect to the dominant measurements in the experimental method, that of the transient pressure and that of the test chamber volume. The methods by which these measurements are made and the roles they play in the data analysis process are discussed further below (for additional discussion see Brehm Thesis, Chapters 4 and 5). Here, consider the general relationships between apparatus geometry and sensitivity to these measurements.

The pressure measurement has an associated maximum uncertainty which is inversely proportional to the pressure change used to initiate the test, $\Delta P$. In order to minimize the effect of this uncertainty on the analysis of the measured transient pressure, it is desirable for the pressure to change as much as possible during the course of the test. Since this pressure change is created by the uptake of the test gas into the foam, it is, in turn, desirable to maximize the foam's capacity for such mass uptake, which amounts to *maximizing the volume of the foam sample* since there is no control over its solubility. Furthermore, for a given mass uptake into the foam sample, the pressure change is inversely proportional to the volume of gas surrounding the foam, so it is desirable like to minimize this volume.

A quick analysis of the analytical results supports these conclusions. FIG. 6 (discussed further below) shows that the change in pressure at a given time $\tau$ increases when the equilibrium sorption parameter G is increased. As discussed below, this parameter represents the ratio of gas storage capacity of the foam sample to that of the surrounding chamber. For a fixed solubility ratio K, this parameter may be increased by increasing the ratio of foam volume to gas volume, $V_f/V_g$.

The data analysis process uses the measured chamber volumes, $V_t$ and $V_g$, only in the form of their ratio $V_t/V_g$. If each of the measurements has some fixed uncertainty which is independent of the size of the chamber volume, the best accuracy will be obtained for large values of this ratio. If we write to total chamber volume as the sum of the gas volume and the foam sample volume, we get $$\frac{V_t}{V_g} = \frac{V_f + V_g}{V_g} = \frac{V_f}{V_g} + 1$$

which indicates that maximizing $V_t/V_g$ and maximizing $V_f/V_g$ are identical goals. The clearest way to achieve this goal is to maximize the sample volume. Since the sample thickness is already determined by time constraints, maximizing the volume means maximizing the sample cross-sectional area A. This area, however, is constrained by sample preparation technique and by the structural integrity of the foam sample, which decreases with larger samples, especially for the small thickness considered. In the case of foam samples, these factors together give an optimal sample diameter approximately 4 cm, which is therefore the inside diameter of the test chamber in accordance with a preferred embodiment of the invention. The two ratios may be optimized still more by minimizing the free space around the sample in the chamber. Therefore the test chamber in accordance with a preferred embodiment of the invention is designed to fit the dimensions of the largest expected foam sample as closely as possible. Smaller samples are supplemented with solid spacers to maintain a high value of $V_f/V_g$. Also, relatively small ⅛ in. O.D. tubing is used and tubing lengths are minimized to further satisfy this goal.

5. Procedure

In accordance with a preferred embodiment of the invention, as described in more detail below, once the sample and chamber are prepared, sealed and connected into the system, the apparatus is allowed to flush for the length of time necessary to establish an equilibrium state in the test chamber. This state is one in which the test gas has permeated the foam completely and all other gases have been removed from the test chamber. The length of time required for this process depends precisely on the permeability which is being measured, so this length of time cannot be known in advance. However, it is easy to check for equilibrium by closing off both the inlet and outlet valves and recording the output of the pressure transducer; if it changes significantly, equilibrium has not been reached. This step of establishing the initial equilibrium state comprises the largest component of time required for any given measurement in this permeability measuring process, and it varies as the square of the sample thickness. Once the initial equilibrium state has been established, the test chamber outlet valve is closed. Then the inlet valve is opened and quickly closed again, allowing the chamber to fill with gas from the test gas reservoir to some new pressure. The transducer output is recorded throughout these valve manipulations, because as soon as the inlet valve is closed again, this pressure will begin to drop and the test is underway. All that remains is to record the pressure in the test chamber as a function of time. The test is completed either when the pressure reaches its equilibrium value, or at some earlier time, depending on the method of data analysis. When the test is complete, the same gas may be tested at a different temperature or another gas may be introduced for testing.

BRIEF DESCRIPTION OF THE DRAWINGS

FIGS. 1A and 1B show a comparison of the effective sample thickness in typical transmission (prior art) and sorption experiments.

FIGS. 2A and 2B show a comparison of the effect of open pathways through the foam sample in typical transmission (prior art) and sorption experiments.

DESCRIPTION OF SPECIFIC EMBODIMENTS

1. Apparatus

Figure 3:
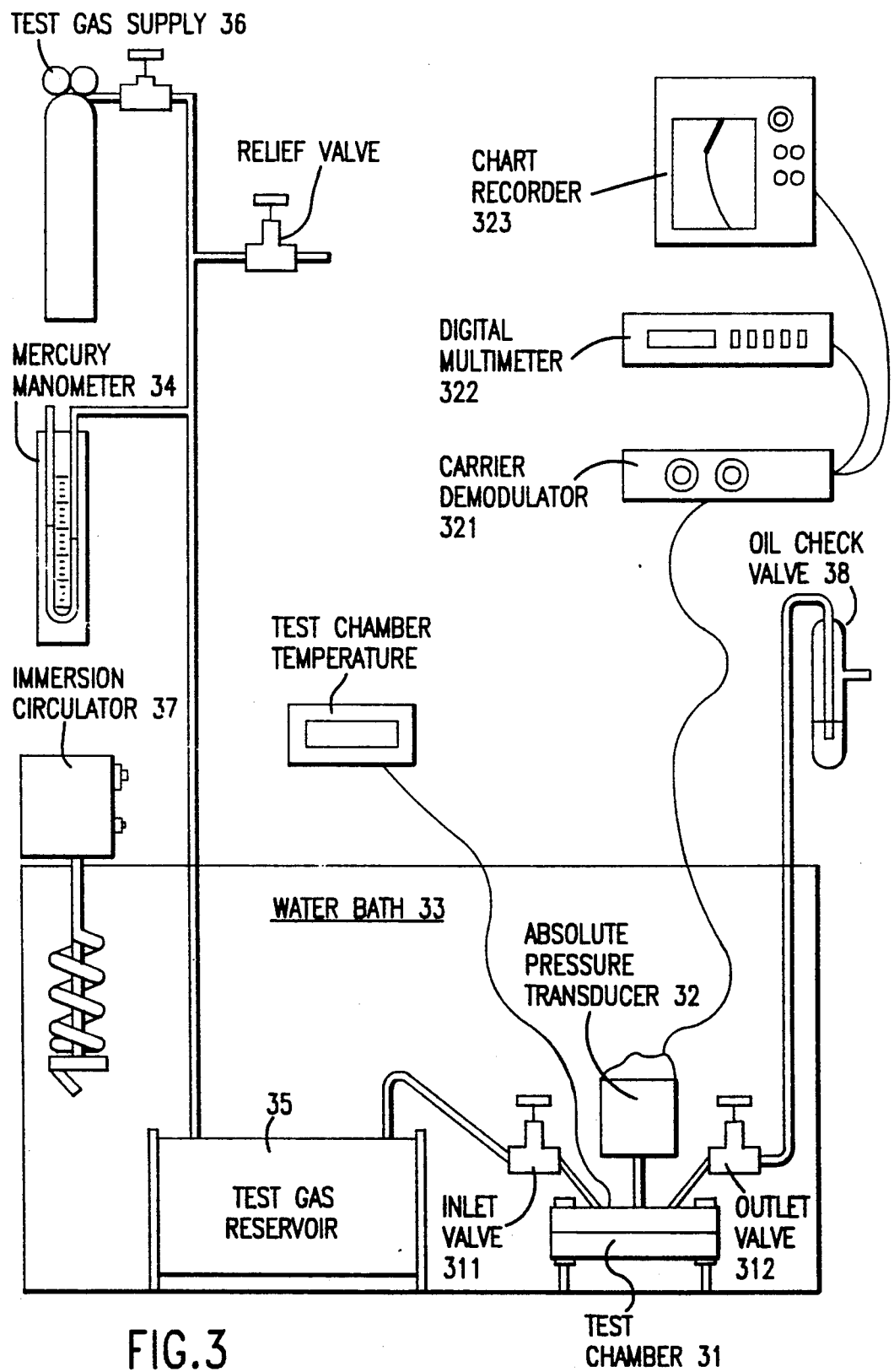
FIG. 3 is a schematic diagram of constant-volume sorption measurement system in accordance with a preferred embodiment of the present invention.
Figure 4:
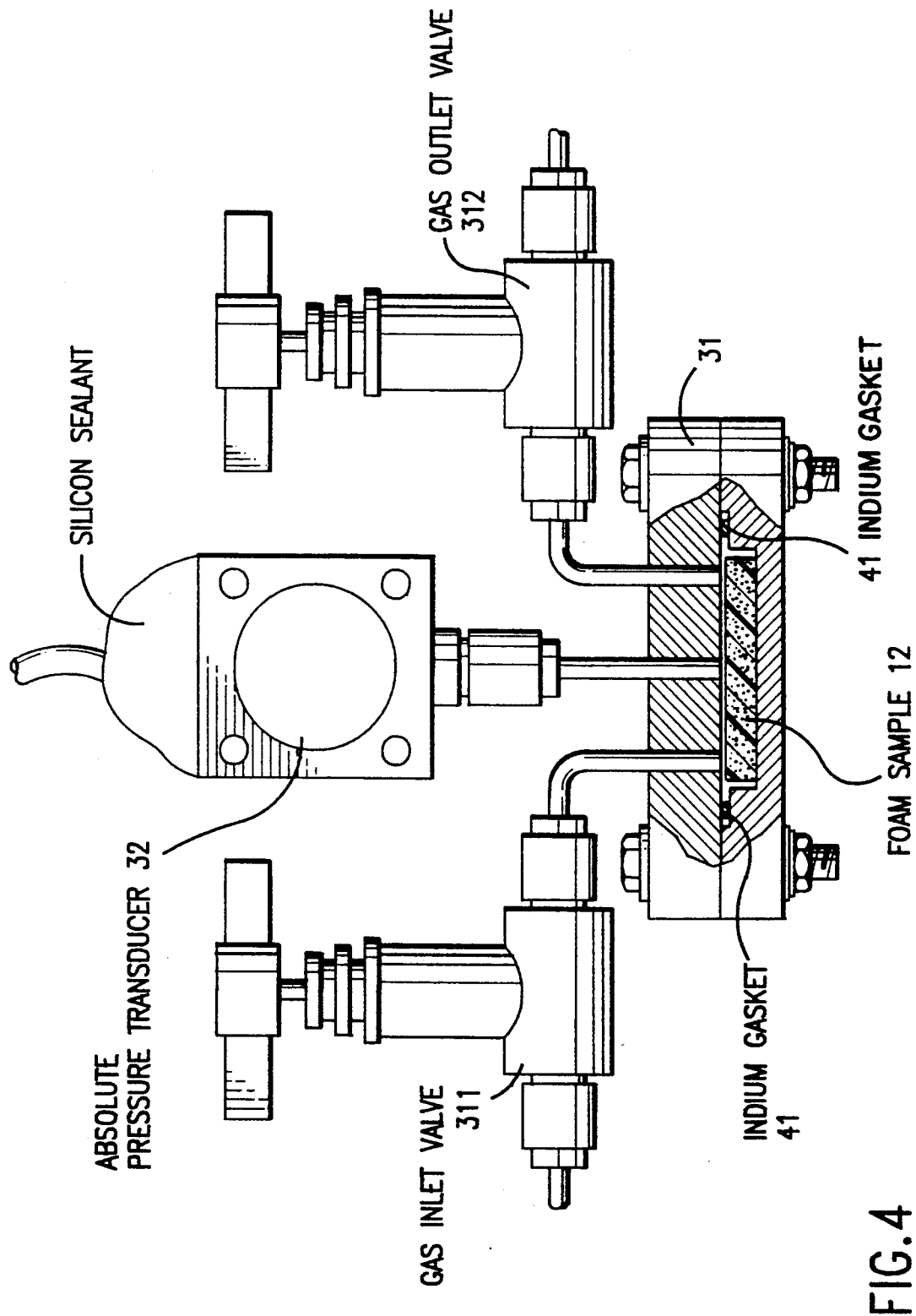
FIG. 4 is a cut-away view of the constant volume test chamber shown in FIG. 3.

The arrangement of equipment used in a preferred embodiment of the present invention is shown in FIG. 3. The central component of the system is the constant-volume test chamber 31, which is shown in more detail in FIG. 4. It has been shown above that the accuracy of the system improves as the ratio of sample volume to void volume is increased. The test chamber 31 is thus designed to maintain a reasonable sample cross-sectional area for structural stability and ease of preparation and to achieve a minimum of void volume surrounding the sample. It is also designed to allow samples in a range of thicknesses in order to take full advantage of the potential for accelerating the tests. The maximum allowable sample thickness is 0.5 cm; thinner samples are supplemented with solid spacers to maintain a low void volume. The maximum sample diameter is 4.0 cm.

The model of the measurement process assumes that once the pressure step is imposed, the chamber 31 is sealed, and the test begins; the total mass in the test chamber then remains constant. The implementation of this assumption requires unusually rigorous sealing in which high vacuum techniques must be applied. The highly-malleable indium gasket 41 provides an essentially impermeable seal and establishes precisely the same total chamber volume on successive closures (see Brehm Thesis). The inlet and outlet valves 311 and 312 have stainless steel bodies and stainless steel ball-joint stem tips for repeated leak-tight closure. The main body of the chamber 31 is machined from stainless steel stock, and the stainless steel tubes are helium arc welded in place. All exposed surfaces are cleaned thoroughly and baked to eliminate outgassing.

The pressure is measured with a Validyne AP-10 variable reluctance absolute pressure transducer 32 with a range from 0 to 20 psia. The transducer 32 is of stainless steel all-welded construction, so with the electrical connections properly sealed it may be submerged in the temperature-controlled water bath 33. In other embodiments, other means can be used to maintain constant temperatures without the use of a water bath. Such means may include placing the apparatus in a high conductivity enclosure which is itself covered with thermal insulation. In conjunction with the Validyne CD-15 carrier demodulator 321, the transducer provides a 0-10 VDC output, magnitude by digital multimeter 322 and chart recorder 323; the transducer has a calibrated accuracy of approximately 1% over the test range of 760 mm Hg to 812 mm Hg (0 to 1 psig). Note that the accuracy of the pressure transducer 32 could be improved dramatically by using a differential transducer with a smaller range referenced to atmospheric pressure or to a tightly-controlled pressure reservoir. The accuracy of the final measurement, however, depends on the accuracy of the pressure reference, which is difficult to maintain. The differential set-up also requires a more complicated plumbing and valve arrangement which is more prone to equipment failure and operator error. In this embodiment, the absolute transducer was selected for its simplicity and high accuracy.

A mercury manometer 34 is used to calibrate the transducer and to set the level of the imposed pressure step to be used in the test. The test gas reservoir 35 submerged in the water bath 33 insures that the test gas from supply 36 has reached thermal equilibrium before it enters the test chamber 31. The water bath with a Lauda B-1 immersion heater/circulator 37 controls the temperature of the thermally-sensitive components to within ±0.03° C. A new version of the system is under development which eliminates the inconvenient water bath by using a custom-designed isothermal chamber with a resistance heater in conjunction with a high-accuracy digital temperature controller to maintain the temperature within ±0.05° C.

2. Test Procedures

Figure 5:
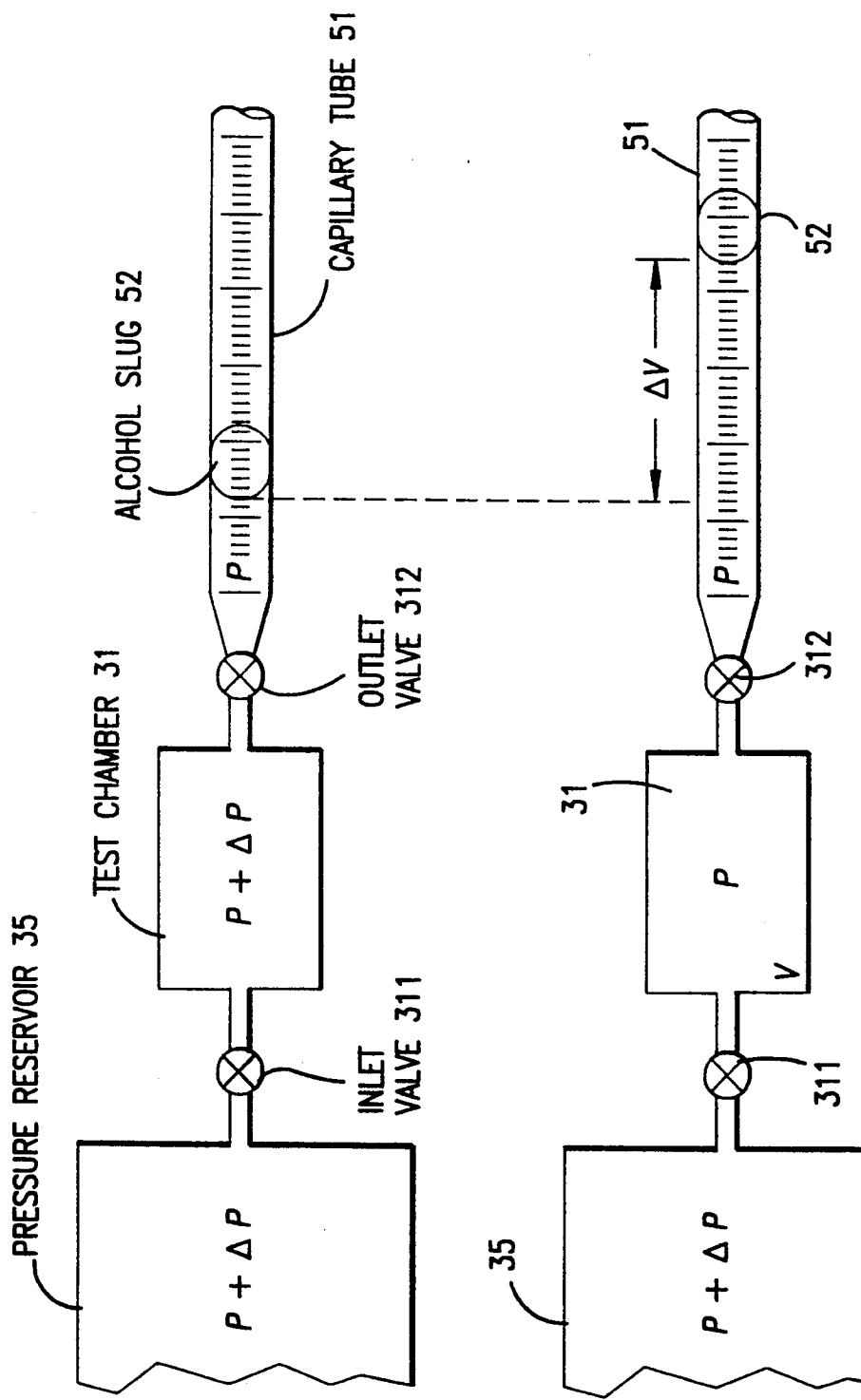
FIG. 5 is a schematic diagram of chamber volume measurement in accordance with a preferred embodiment of the present invention.

For each sample tested, the volume of the test chamber is measured first without the sample in place and then with the sample sealed in the chamber. The difference between the two measurements gives the sample volume, which is combined with a measurement of the sample diameter and an assumption of cylindrical geometry to calculate an effective sample half-thickness L. This means of determining L factors out any open cells on the surface of the sample. To perform the volume measurement, the oil check valve 38 in FIG. 3 is replaced by a graduated pipette with an alcohol slug in it, as shown schematically in FIG. 5. With the chamber outlet valve closed, the inlet valve is opened to raise the pressure in the chamber to the reservoir pressure of P+ΔP, where P is the atmospheric pressure at the time of the measurement. Then the inlet valve is closed and the outlet valve is opened, allowing the chamber gas to expand back to pressure P as it moves the slug by a volumetric amount of ΔV. The chamber volume is then calculated using Boyle's Law as $$V = P\Delta V/\Delta P.$$

Before a test begins a known equilibrium state is established in the chamber. The outlet valve 312 is opened and the inlet valve 34 is throttled to allow the test gas to flush through the chamber at atmospheric pressure. This process allows the test gas to fully permeate the sample and it allows any other gas species which may have been in the sample to diffuse out. In order to determine when complete equilibrium has been achieved, the inlet and outlet valves 311 and 312 are both closed and the chamber pressure is monitored. If the pressure remains steady, equilibrium has been established and the test may begin. If the pressure changes this indicates the existence of non-equilibrium conditions in the chamber, so flushing is resumed.

The present invention also permits a sample to be initially conditioned outside the apparatus in any suitable closed container. That is, the sample can be placed in such a closed container, maintained at a desired temperature, and flushed with test gas so as to permeate the sample and permit any other gas species in the sample to diffuse out. The sample can then be transferred to the apparatus of the present invention under similar pressure and temperature conditions, and tested in the manner set forth in the previous paragraph to assure that the sample is in an equilibrium state. When equilibrium is established, the sample can be tested using the procedures set forth below. Employing the present strategy means that the test apparatus does not have to be used for initial conditioning and can be utilized more productively in instances wherein multiple tests are being conducted.

To initiate the sorption test, the outlet valve 312 is closed and then the inlet valve 311 is briefly opened to impose a step pressure change of $\Delta P$ at the surface of the sample. The inlet valve 311 is quickly closed again, establishing the chamber constant volume. The chamber pressure is recorded from the time just before the step pressure is imposed until the pressure returns to equilibrium.

If another test is to be run with the same gas at a different temperature, the chamber 31 is kept sealed while the temperature is changed. It is important to note that when thermal equilibrium is reached at the new temperature, the gas concentration in the sample and the chamber *will still be in equilibrium* so the time required for the flushing process for this second test is avoided.

3. Data Analysis a. Basic Model

Fick's Law with constant diffusion coefficient and Henry's Law with constant solubility coefficient are used to model the gas transport in the foam. It is assumed that the sample is large enough to allow treatment as a homogeneous continuum which is characterized by effective diffusion and solubility coefficients. With sealed edges the sample may be treated as a plane sheet of cross-sectional area A and half-thickness L immersed in a limited volume of test gas. The test begins with uniform concentration $C_1 = SP_1$ in the sample and uniform concentration $C_2 = S(P_1 + \Delta P)$ in the void volume V surrounding the sample. The chamber is completely sealed so the total mass in the chamber remains constant throughout the test.

The method of solution for this geometry and these boundary conditions is given by Wilson, A. H., "A Diffusion Problem in which the Amount of Diffusing Substance is Finite," *Philosophical Magazine*, 39, 48 (1948). The non-dimensional chamber pressure $\overline{P} = (P - P_1)/\Delta P$ is given by the expression $$\overline{P} = \frac{1}{G+1} + \sum_{n=0}^{\infty} \frac{2G}{G(G+1) + a_n^2} e^{-a_n^2 \tau}$$

where the $a$ are the real, positive roots of the equation $$a_n + G \tan a_n = 0.$$

Figure 6:
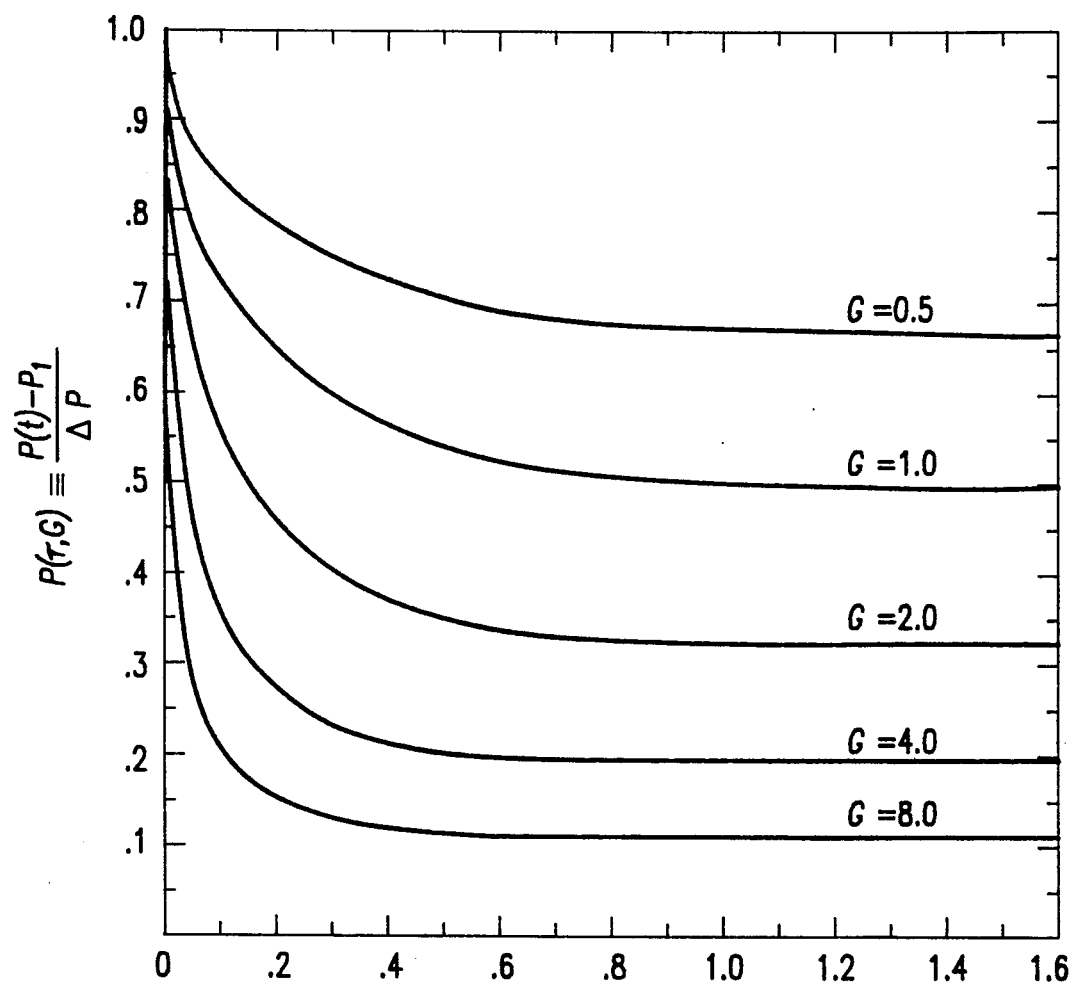
FIG. 6 is a plot of analytical solution showing chamber pressure $\bar{P}(\tau,G)$ for a range of G.

The variable $\tau = Dt/L^2$ represents the characteristic time scale of the diffusion process and verifies the proportionality to the square of the sample thickness. The equilibrium sorption parameter $G \equiv 2ALS/(V/RT)$ represents the ratio of the gas storage capacity of the sample in the cell interior and in the cell walls and struts to that of the void volume surrounding the sample.

b. Determination of S and D:

A plot of $\overline{P}$ for several values of G is shown in FIG. 6. From the measured equilibrium pressure $\overline{P}_\infty = 1/(G+1)$ the value of G for the test is calculated.

Using the definition of G the solubility coefficient is then calculated as $$S = \left(\frac{1}{\overline{P}_\infty} - 1\right) \left(\frac{V/RT}{2AL}\right).$$

Figure 7:
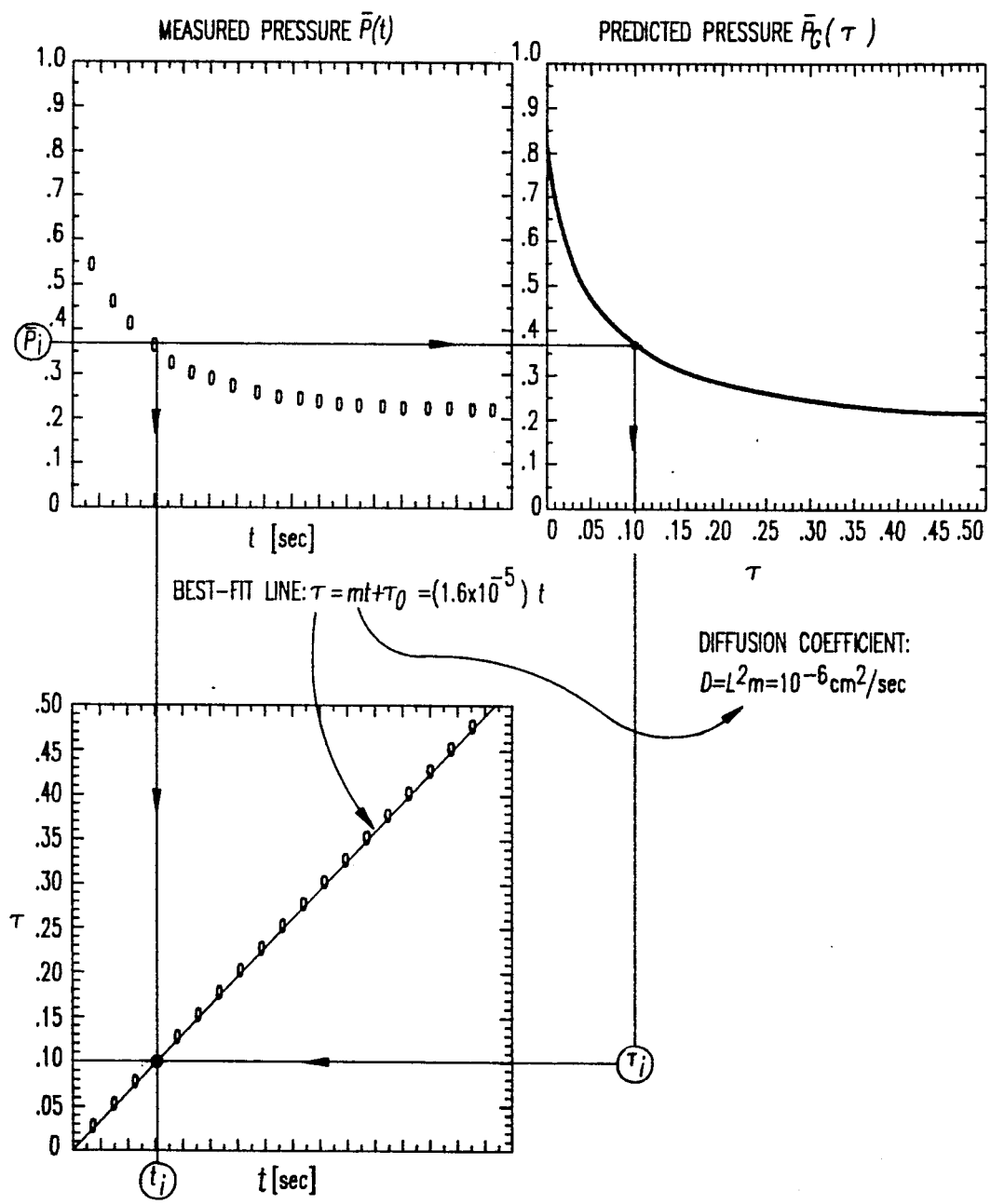
FIG. 7 is a diagram of mapping from B(t) and $B_G(\tau)$ curves to the $\tau$ vs. t plane. The numbers correspond to an ideal case with G=4.0, L=0.25 cm, and D=$10^{-6}$ cm$^2$/sec.

The value of G is used to generate a characteristic curve which is then matched with the transient data points to determine the diffusion coefficient. FIG. 7 illustrates this matching process. For each measured pressure $\overline{P}(t)$ the predicted curve is consulted to find the value of $\tau$ which gives the same value of $\overline{P}$. By virtue of the definition of $\tau$, a plot of the $(t,\tau)$ pairs gives a straight line with slope $m = D/L^2$ so the diffusion coefficient is found as $$D = L^2 m.$$

Figure 8:
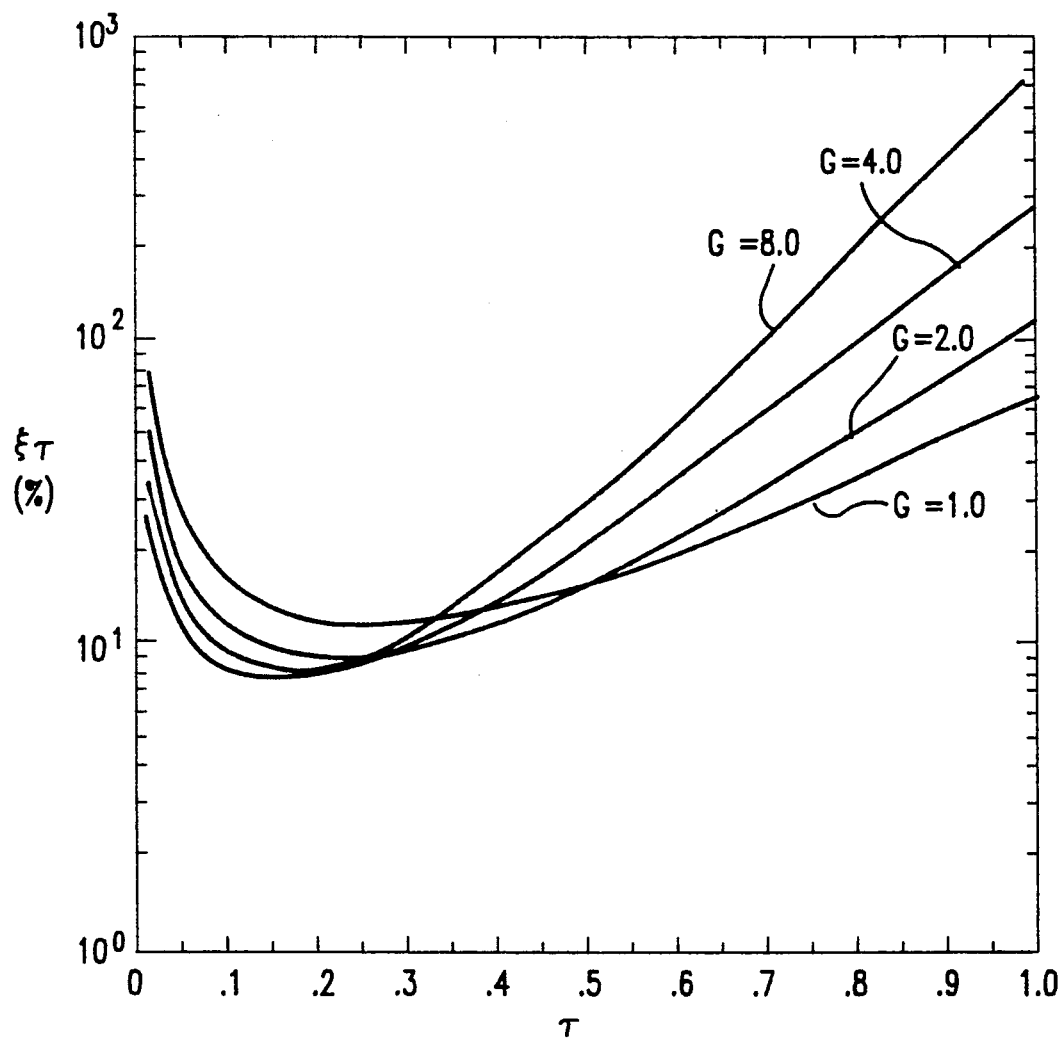
FIG. 8 is a graph of percent uncertainty in $\tau(t)$ as a function of $\tau$ and G, as determined by a single data point. The ultimate uncertainty in the value of D determined from a set of data points from the range $0.03 \leq \tau \leq 0.50$ is approximately +6%.

This process provides the best evaluation of D by incorporating all of the transient data points.

c. Accelerated Determination of D:

When the foam effective solubility can be estimated in advance, either by extrapolating from a completed test at a different temperature or by some knowledge of the normal behavior of the gas (for example, the air components generally have "very low" solubility in the polymer, so the foam effective solubility is approximately what it would be if the sample were all cell gas), this information may be used to determine D without waiting for the test to reach equilibrium. In this case the value of G and the corresponding characteristic curve are generated in advance such that D may be calculated as the transient data is collected. A typical test like this need only continue to $\tau \approx 0.25$ to produce reliable results, providing a four-fold savings over normal tests employing the present invention.

d. Estimate of Uncertainty:

The accuracy of both D and S improve with higher values of G, which are achieved by increasing the ratio of sample volume to void volume. For the measurements of blowing agent solubility, the test chamber gave a value of $G \approx 1.6$ which gives an uncertainty in S of approximately ±2% on a 95% confidence interval. The accuracy of D as calculated from a single data point further depends on the time at which the data point was measured. FIG. 8 shows $\tau$, the percent uncertainty in the value of $\tau$ determined from the matching process, as a function of time for several values of G. After using the slope of a best-fit line to determine D, the uncertainty depends on the number of data points used, the distribution of these points, and the range of $\tau$ from which these points are taken. A typical test of $N_2$ had $G = 2.8$ and used 22 data points in the range $0.03 \leq \tau \leq 0.50$ to produce an uncertainty in D of approximately ±6% on a 95% confidence interval.

e. Two-Dimensional Analysis:

For all results presented here, the sample edges were sealed with an impermeable epoxy to allow one-dimensional (plane sheet) analysis of the diffusion process. For added convenience, it is desirable to eliminate the need for this epoxy by providing a two-dimensional (cylindrical) analysis of the process. An analytical solution for the cylindrical geometry and constant volume boundary condition does not exist and a numerical solution is cumbersome and slow. Instead we may deduce the behavior of the cylindrical case by analogy to the same geometry with a constant pressure boundary condition, for which both the one-and two-dimensional analytical solutions are readily computed. The best analog between the constant pressure and constant volume cases is the normalized mass uptake into the sample, $M^*(t)=(M(t)-M_0)/(M_\infty-M_0)$, where $M(t)-M_0$ is the mass diffused into the sample at time t and $M_\infty-M_0$ is the total mass added to the sample during the test. Using this analogy, we assume that the ratio $M^*_{2D}/M^*_{1D}$ is the same for the two boundary conditions, so that the mass uptake for the cylindrical constant volume case is predicted by $$(M^*_{2D})_{CV} \approx (M^*_{2D}/M^*_{1D})$$
$$_{CP}(M^*_{1D})_{CV} = R_M(M^*_{1D})\ _{CV}.$$

Figure 9:
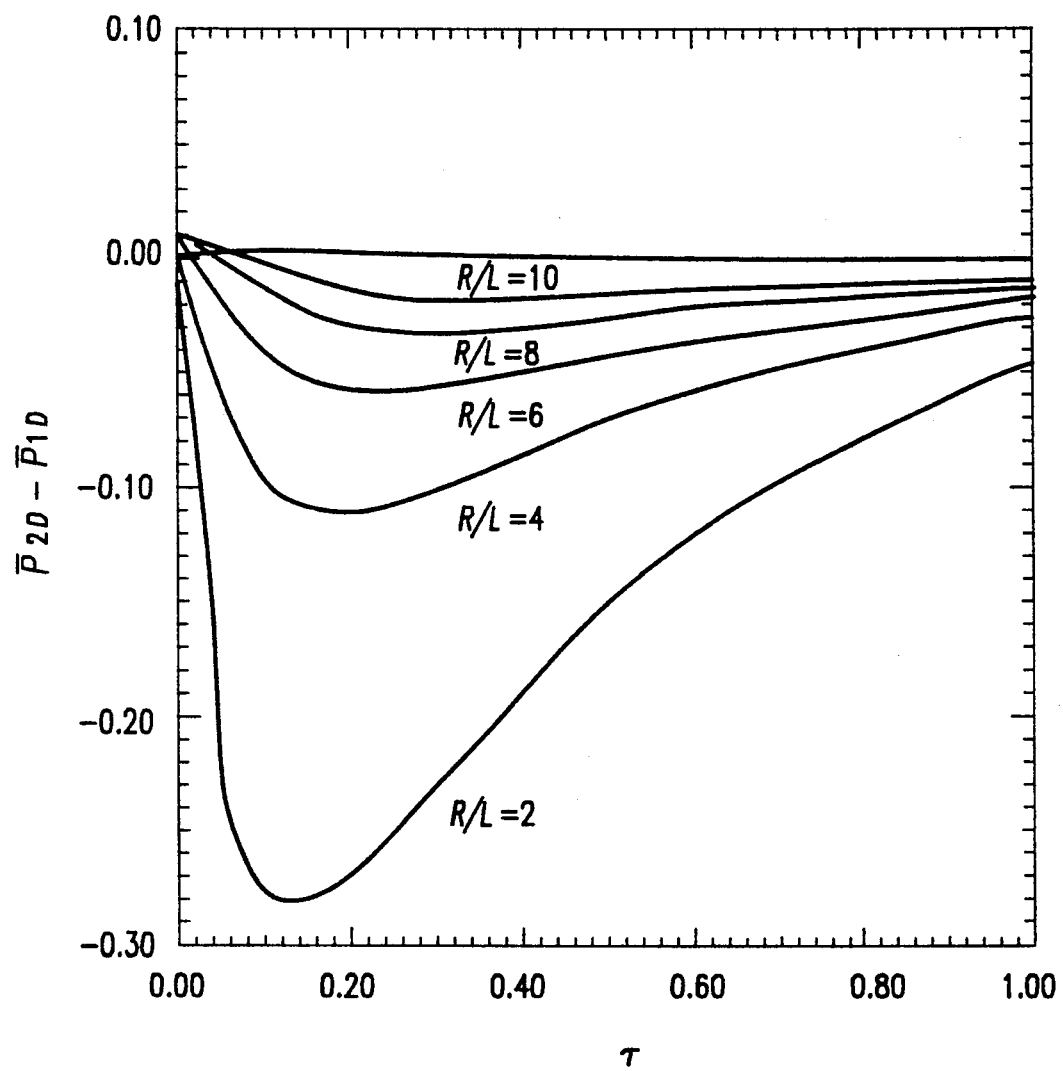
FIG. 9 is a graph of the difference between cylindrical (2D) and plane sheet (1D) solutions for non-dimensional chamber pressure as a function of $\tau$ with R/L as a parameter and with G×2.5.

Solutions from Crank, J., *The Mathematics of Diffusion*, Oxford University Press, Oxford, UK, 1956, for the constant pressure boundary condition cases can be easily adapted to compute the ratio $R_M$ as a function of $\tau$ with aspect ratio R/L as a parameter. Rearranging terms to express $\bar{P}_{2D}$, the desired non-dimensional chamber pressure for the cylindrical constant volume case, we get $$\bar{P}_{2D} = R_M(\bar{P}_{1D}-1)+1,$$

where $\bar{P}_{1D}$ is the analytical solution for the one-dimensional constant volume case. The difference between $\bar{P}HD$ 2D and $\bar{P}_{1D}$ can be used either as a correction to the one-dimensional analysis to apply to cylindrical diffusion or as a guideline for maintaining a low enough aspect ratio to allow straight one-dimensional analysis. FIG. 9 shows a plot of this difference as a function of $\tau$ with R/L ranging from 2 to 10 for a case with G=2.5. The samples used in this research have R/L between 8 and 12, which would give maximum pointwise error of approximately 3% (if the edges had not been epoxied); the ultimate error induced in D would be considerably less.

f. Correction for Sample Deformation:

The basic model of the test process includes the assumption that the foam sample remains rigid throughout the test and therefore preserves the constant volume of both the sample and the surrounding chamber. In reality the sample will deform slightly due to the total pressure difference between the gas inside the foam cells and the gas in the test chamber surrounding the foam. The deformation will be greatest immediately after the pressure change is introduced, and it will decrease as the test gas permeates the sample and the pressure approaches equilibrium again, at which point the sample will return to its original undeformed shape (barring non-elastic deformation).

The magnitude of the deformation depends on the magnitude and a sign of $\Delta P$ and the geometry of the sample and the test chamber. With a positive $\Delta P$ less than about 400 mm Hg, the sample may be assumed to undergo elastic compression, the magnitude of which is limited by the Poisson ratio of the foam's polymer structure and the gas pressure in the foam cells. Using the analysis and correlations given by Gibson, G. L. and Ashby, H. F., Cellular Solids: Structures and Properties, Pergamon Press, Oxford, UK, 1988, we predict a volumetric compression of approximately 2% and 13% with applied pressure differences of 52 mm Hg and 356 mm Hg, respectively. The actual deformations in these two cases, as measured by the pycnometer-type method described above, were 1% and 5%, which give support to the assumption of elastic compression, although they are significantly smaller than the predicted values.

Sample deformation has two distinct effects on the analysis of the measured chamber. First, the deformation at the start of the test increases the initial mass in the chamber and thereby affects the calculation of G and S from the equilibrium pressure $\bar{P}_\infty$. This effect is corrected for by performing the chamber volume measurement with the same size $\Delta P$ as is used in the test, which gives the void volume with maximum sample deformation, $V_{gm}$. Further measurements with successively smaller values of $\Delta P$ are used to extrapolate to the void volume with no sample deformation, V. Combining these measurements in a mass balance at t=0 and $t\to\infty$ gives a corrected expression for the equilibrium pressure:

$$\bar{P}_{\infty,d} = \left[\frac{V_{gm}}{V}\left(1+\frac{P_1}{\Delta P}\right)-\frac{P_1}{\Delta P}\right]\frac{1}{G+1} = R_d\bar{P}_\infty.$$

For the earliest measurements made with this system, a pressure step of $\Delta P=356_{mm}Hg$ was used and the deformed volume ratio was measured as $V_{gm}/1.05$, giving a correction factor of $R_d=1.16$. In all other measurements, a pressure step of $\Delta P=52$ mm Hg was used and no measurable deformation occurred.

Figure 10:
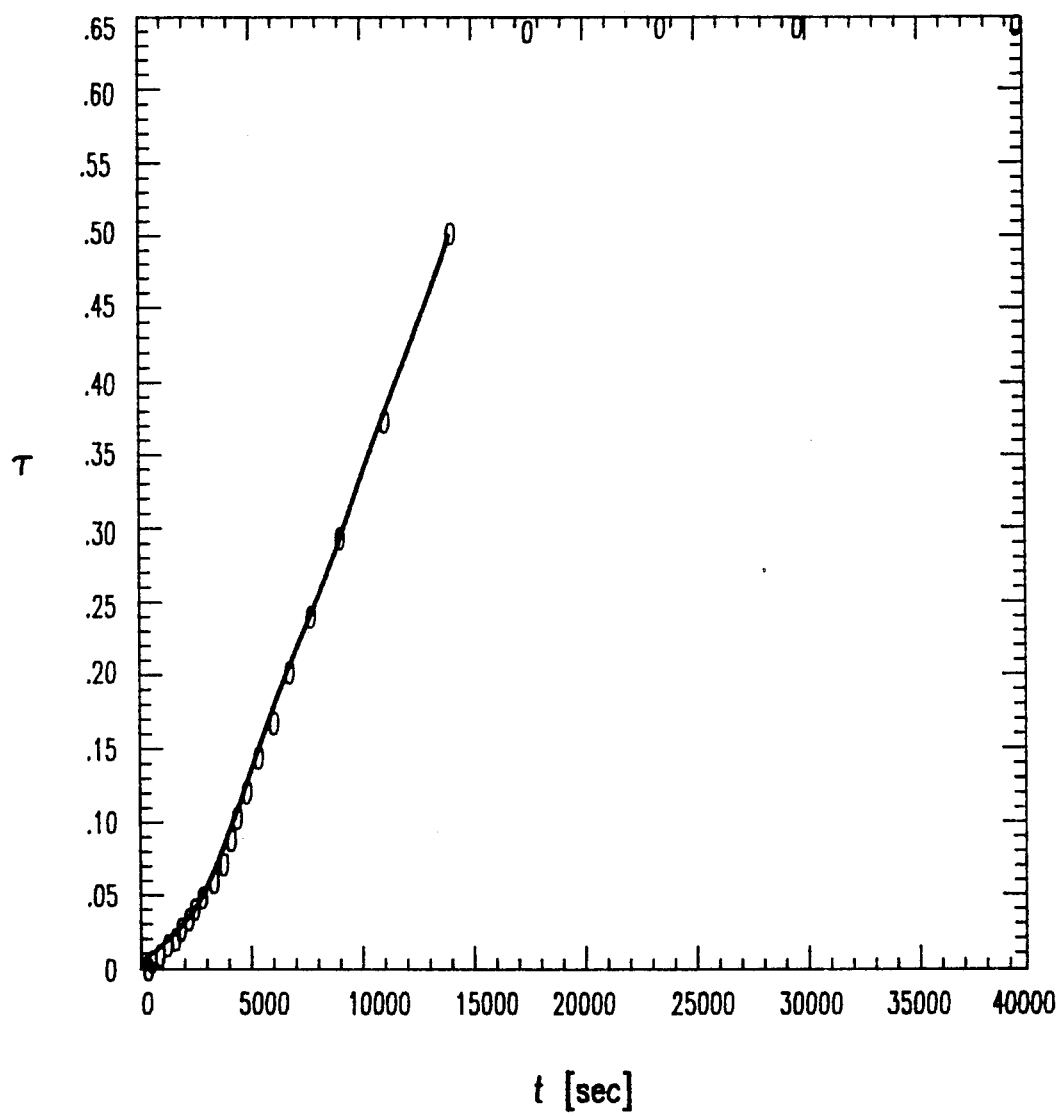
FIG. 10 graphs a plot of $\tau$ vs. t for a test with significant sample deformation.
Figure 11:
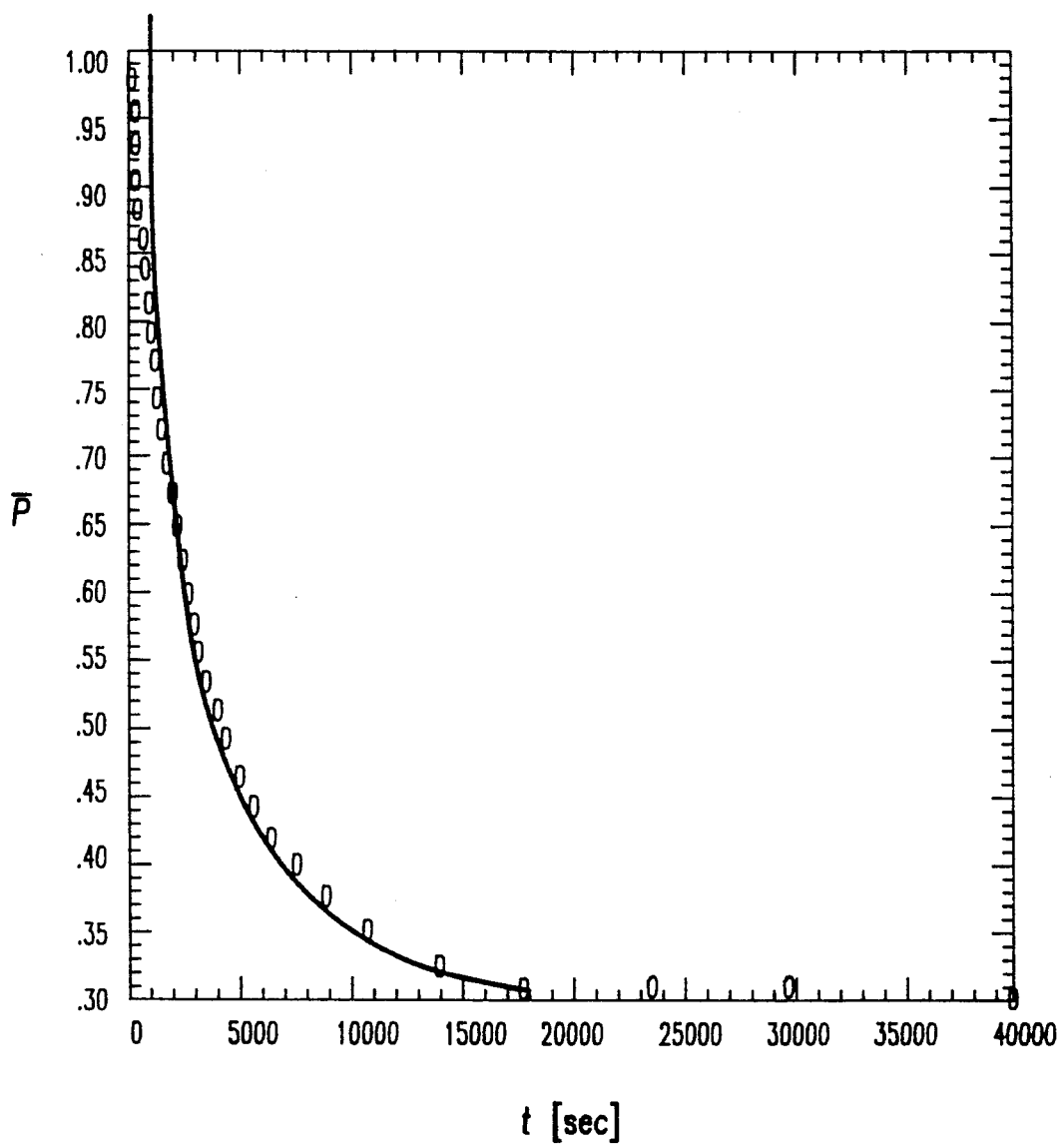
FIG. 11 shows a comparison of measured pressure and predicted pressure for a test with significant sample deformation.

The second effect of sample deformation is its influence on the diffusion coefficient derived from the transient pressure. The decrease in the chamber void volume as the sample expands and the increased pressure gradient caused by the initial compression of the sample both cause the chamber pressure to drop more slowly than it would with a rigid sample. FIG. 10 shows a $\tau$ vs t plot for the test mentioned above with $R_d=1.16$. The shape of the "tail" on the curve at short times indicates a lower apparent diffusion coefficient in this region as expected, but the effect is limited to $\tau<\sim 0.05$. If we determine D using only data points from the linear portion of the curve, we will obtain an accurate measure of D and an effective offset in the t=0 point on the curve. If this offset is used in conjunction with the diffusion coefficient to generate a predicted pressure curve, it will fit the data poorly for short times but quite well for larger times, as shown in FIG. 11. The worst case error incurred by ignoring this effect may be estimated by computing the diffusion coefficient from the slope of a line from the origin to a single data point, say at $\tau=0.5$, in FIG. 10. Applying this method to all of the tests performed with significant sample deformation, the maximum error in an uncorrected computation of D would have been 7%.

4. Results

The accuracy and speed of the constant-volume sorption method has been demonstrated by collecting data on polyurethane foam, the general properties of which are given in Table 2. The foam was tested with $CO_2$, $O_2$, $N_2$, and R11, each at 40° C., 60° C., and 80° C. The tests of the air components were performed using a sample with a diameter of 3.98 cm and a thickness of 0.50 cm. The tests of R11 used a sample with a diameter of 3.88 cm and a thickness of 0.30 cm.

The diffusion coefficients calculated for each gas and temperature combination are shown in Table 3. Several of the test were run two or more times and showed a repeatability within 4%. The measured effective solubility coefficient of R11 at 80° C. was 1.33 cm$^{3stp}$/cm$^3$atm. Using the foam properties from Table 1, this figure converts to an R11 solubility in the solid polymer cell walls of 10% by weight. Using correlations from Van Krevelen, D. W., Properties of Polymers: Their Estimation in Correlation with Chemical Structure, Elsevier Scientific Publishing Co., New York, 1976, this may be extrapolated to 14% at 40° C. and 17% at 25° C. The solubility of the air components in the solid polymer is too low to allow accurate measurement on a foam sample.

A 0.76 cm-thick sample of the same foam was evaluated using a high-accuracy steady-state transmission apparatus similar to that described by Ostrogorsky and Glicksman, "Rapid, Steady-State Measurement of the Effective Diffusion Coefficient of Gases in Closed-Cell Foams", *Transactions of the ASME*, vol. 110, p. 500 (1988). Measurements were made with $CO_2$, $O_2$, and $N_2$ at 30° C., 40° C., 50° C., and 60° C. This device gives the permeability coefficient, so the values of D and S from the sorption measurements are multiplied to get Pe for comparison purposes. The two sets of data are plotted in FIG. 12 as a function of temperature. All of the data points fit well with the expected Arrhenius temperature dependence. Using this temperature dependence to extrapolate as necessary, the mean deviation between the sorption and transmission data is found to be 5.6%.

Figure 12:
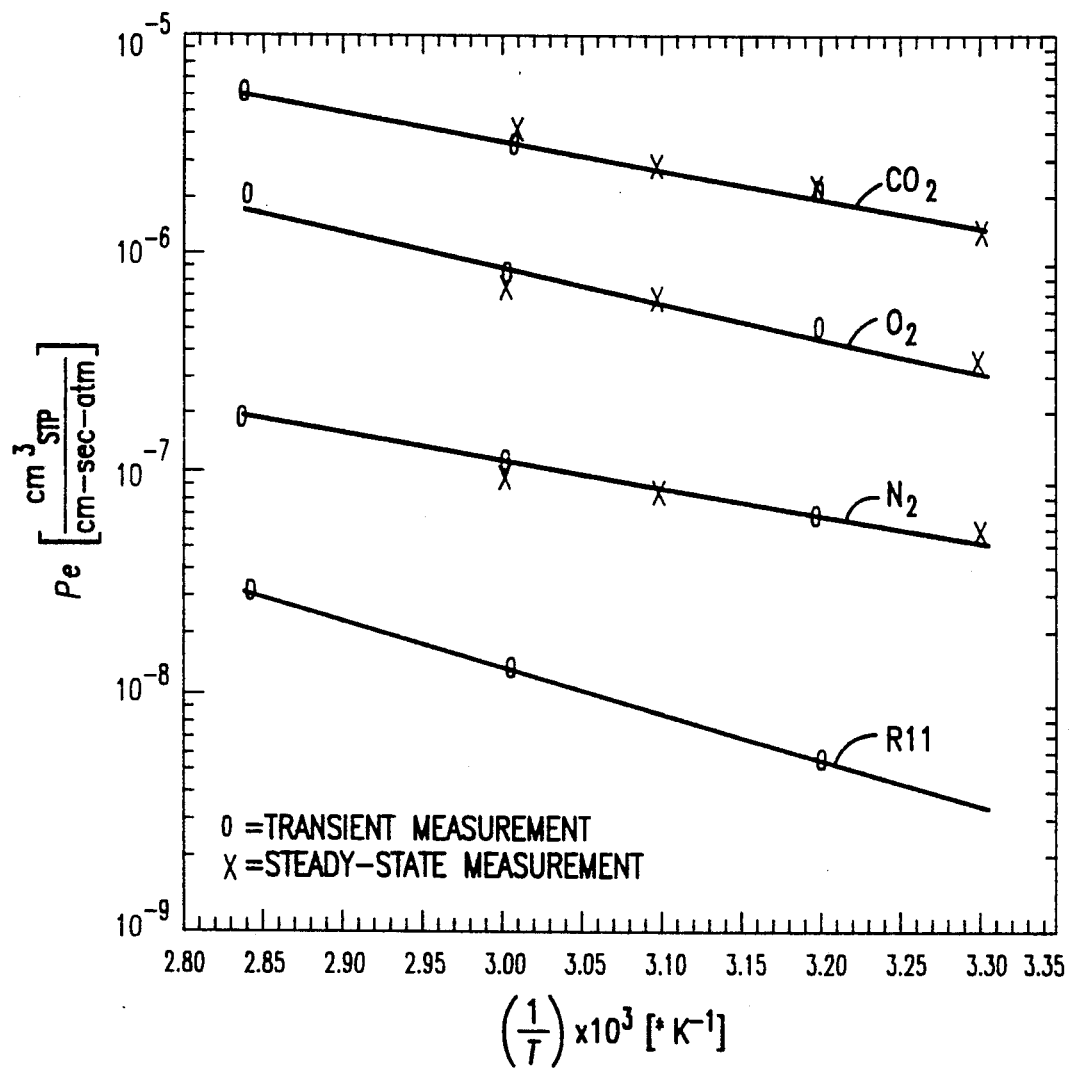
FIG. 12 graphs the resultant permeability coefficients for polyurethane foam as derived from sorption (transient) and transmission (steady-state) measurements.

The relative speed of the sorption technique can be appreciated in general terms by the fact that all of the sorption tests represented in FIG. 12, including many repeated tests and the very slowly-permeating R11, required approximately the same time to collect as the much less extensive transmission data. Based on the sample sizes used, a typical series of identical tests would be completed about 8 times faster using the sorption techniques. If none of the tests were repeated, the sorption data in FIG. 12 would have required approximately 4-5 weeks to complete. If one were willing to extrapolate the data points at 40° C. from those at 60° C. and 80° C., this time could be reduced to about 2-3 weeks. Finally, the time may be reduced even further if the sample under test has a higher diffusion coefficient than the samples tested here, which is true of many insulation and packaging foams.

What is claimed is:

1. An method of measuring the gas permeability of a cellular polyureic composition, comprising:
   i) obtaining a thin sample of the composition, determining the volume of the sample, and sealing the sample in a constant-volume test chamber of known volume;
   ii) surrounding the sample with a test gas, and allowing the test gas to reach equilibrium at an initial pressure with the gas inside the sample;
   iii) rapidly changing the pressure of the surrounding test gas and sealing the test chamber;
   iv) observing the change in pressure of the surrounding test gas over time; and
   v) calculating a quantity related to the equilibrium sorption parameter of the composition from the observed change in gas pressure.

2. A method according to claim 1, wherein step (iv) is discontinued before the test gas reaches equilibrium with the gas inside the sample and step (v) includes the step of using known solubility characteristics of the composition in connection with the observed change gas pressure to determine a quantity related to the gas diffusion constant of the composition, whereby testing time is reduced.

3. A method according to claim 1,
   wherein steps (ii), (iii), and (iv) include the step of maintaining the test chamber at a first temperature, and step (iv) is continued until the test gas reaches equilibrium with the gas inside the sample, and
   further comprising the step of repeating steps (iii) and (iv) while maintaining the test chamber at a second temperature and step (iv) at the second temperature is discontinued before the test gas reaches equilibrium with the gas inside the sample, and
   wherein step (v) includes the step of using a quantity related to the equilibrium sorption parameter determined from the observed pressure change at the first temperature to determine a quantity related to the gas diffusion constant of the composition.

4. A method according to claim 3, wherein the first temperature is higher than the second temperature.

5. A method according to claim 3, further comprising the step of maintaining the test chamber sealed while changing the test chamber's temperature from the first temperature to the second temperature, whereby the test gas may reach equilibrium with the gas inside the sample without need for the additional expenditure of time consumed by flushing the sample.

6. A method according to claim 1, wherein the sample is a cellular polymeric material and step (i) further includes the step of preparing the sample to have a thickness that is substantially less than 30 cell diameters.

7. A method according to claim 1, wherein step (i) includes the step (a) of configuring the sample within the test chamber in such a way as to minimize the free volume of test gas in the test chamber.

8. A method according to claim 7, wherein step (a) includes the steps of configuring the sample and the test chamber to have cross sections of similar geometry and size and to provide a solid spacer between a face of the sample and an internal face of the test chamber.

9. A method according to claim 7, wherein the cross section is circular.

10. A method according to claim 1, wherein the step of determining the volume of the sample in step (i) includes the steps of (vi) causing at least one of the pressure or volume of gas in the test chamber to change by a known amount, measuring the consequent change in pressure-volume conditions in the chamber, and (vii) using Boyle's Law to determine the free volume of test gas in the chamber.

11. A test chamber for measurement of gas permeability of a sample, comprising:
    a pair of mating upper and lower plates, the upper plate having an upper outside face and a mating surface and the lower plate having a lower outside face and a mating surface, the mating surfaces being in contact with one another when the plates are mated;
    the plates so shaped as to define when mated an interior chamber, the volume of the chamber being not substantially greater than the volume of the largest sample to be tested;
    a recess in the mating surface of one of the plates surrounding the wall of the chamber for receiving a gasket;
    a malleable metal wire gasket disposed in the recess;
    means for urging the mating surfaces of the upper and lower plates against one another so as to substantially prevent leakage of test gas from the chamber;
    input means for supplying test gas to the chamber and for valving off such supply;

outlet means for removing gas from the chamber and for valving of such removal;

means for monitoring gas pressure in the chamber;

means for maintaining the chamber at a desired temperature for the duration of a measurement test; and volume change means for minimizing free volume in the chamber not occupied by the sample.

12. A test chamber according to claim 11, wherein the volume change means includes a solid spacer.

* * * * *

UNITED STATES PATENT AND TRADEMARK OFFICE
CERTIFICATE OF CORRECTION

PATENT NO. : 5,157,960

DATED : October 27, 1992

INVENTOR(S) : Brehm and Glicksman

It is certified that error appears in the above-identified patent and that said Letters Patent is hereby corrected as shown below:

In column 17, line 46, the word "polyureic" should read "polymeric".

Signed and Sealed this

Sixteenth Day of November, 1993

BRUCE LEHMAN

*Attest:*

*Attesting Officer*     *Commissioner of Patents and Trademarks*